US006873919B2

United States Patent
Remmlinger et al.

(10) Patent No.: US 6,873,919 B2
(45) Date of Patent: Mar. 29, 2005

(54) METHOD AND DEVICE FOR MACHINE DIAGNOSIS, ESPECIALLY FOR TRANSMISSION DIAGNOSIS

(75) Inventors: Hubert Remmlinger, Friedrichshafen (DE); Robert Ingenbleek, Kressbronn (DE); Gabriele Schuwerk, Ravensburg (DE); Rolf Schmitz, Friedrichshafen (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 0 days.

(21) Appl. No.: 10/612,681

(22) Filed: Jul. 2, 2003

(65) Prior Publication Data

US 2004/0107074 A1 Jun. 3, 2004

(30) Foreign Application Priority Data

Jul. 9, 2002 (DE) .......................... 102 30 757

(51) Int. Cl.[7] .............................................. G01B 7/00
(52) U.S. Cl. .................. 702/38; 73/53.01; 73/53.05; 324/200
(58) Field of Search ............... 702/38; 73/53.01, 73/53.05, 53.07, 61.42, 61.71, 54.18, 649; 324/204, 200, 207.13, 207.2, 207.21

(56) References Cited

U.S. PATENT DOCUMENTS

| 4,219,805 A | * | 8/1980 | Magee et al. ............... 340/631 |
| 5,790,246 A | * | 8/1998 | Kuhnell et al. ............... 356/72 |
| 6,435,013 B1 | * | 8/2002 | Rodriguez et al. ......... 73/61.75 |

FOREIGN PATENT DOCUMENTS

| DE | 29 31 412 | 2/1981 | .......... G01N/27/74 |
| DE | 38 40 430 A1 | 6/1989 | .......... G01F/23/30 |
| DE | 100 58 844 A1 | 6/2002 | .......... G01M/13/00 |
| GB | 2 029 580 A | 3/1980 | .......... G01N/27/72 |
| JP | 10082780 A | 3/1998 | .......... G01N/33/28 |
| WO | 02/46744 A2 | 6/2002 | .......... G01N/33/00 |

\* cited by examiner

*Primary Examiner*—John Barlow
*Assistant Examiner*—Hien Vo
(74) *Attorney, Agent, or Firm*—Davis & Bujold, P.L.L.C.

(57) ABSTRACT

A method for machine diagnosis and, in particular, for transmission diagnosis of a machine or motor vehicle. The measurement system comprises a capturing magnet (2), on the surface of which the ferritic wear particles (3) to be detected accumulate. A binary measurement signal is produced by a reed contact (1) arranged opposite the capturing magnet (2). This measurement gives an indication of the condition of the machine or transmission.

12 Claims, 1 Drawing Sheet

METHOD AND DEVICE FOR MACHINE DIAGNOSIS, ESPECIALLY FOR TRANSMISSION DIAGNOSIS

FIELD OF THE INVENTION

The present invention concerns a method for machine diagnosis and, in particular, for diagnosis of a machine or transmission of a motor vehicle. In addition the invention concerns a device for implementing the method.

BACKGROUND OF THE INVENTION

In modern machines and vehicle transmissions it is nowadays sought to fill these with engine oil and transmission oil once during their lifetime, and the life of such a transmission being, for example, typically on the order of 1 million kilometers.

The machine or transmission oil serves to lubricate and cool all the mechanical elements. Since it is never changed, it is exceptionally suitable for machine or transmission diagnosis since, over the course of time, all kinds of abrasion particles accumulate in the oil. Consequently, analysis of the machine or transmission oil provides information about the condition of the machine or transmission.

In this, ferritic wear is of particularly great importance since in almost any type of incipient damage, such as roller bearing wear, the formation of pitting in the gear teeth leading to tooth fracture, wear of the gear cage bolts, etc., ferritic wear alone, or in combination with other types of wear (non-ferrous metal wear, molybdenum degeneration, etc.), occurs.

In the state of the prior art, there now exists an oil diagnosis system disclosed by the present applicant in WO 02/46744, which detects ferritic wear metals by means of a wear sensor based on the Hall effect. This measurement system is in an oil duct of a transmission or a machine. It is designed as a sensor in a two-part sensor housing. A Hall sensor is arranged in the upper part of the sensor housing. The Hall sensor detects the ferritic wear particles which accumulate on the capturing magnet in the lower part of the sensor housing.

Such oil diagnosis systems are undergoing continual further development because, for example, the assembly of the two-part housing in the oil duct is relatively difficult to carry out. Further development potential is available in the design of the sensor's electrical supply. For example, it is extremely important to keep the supply voltage of the Hall sensor stable so that there will be no fault-inducing fluctuations in the measurement signal.

Accordingly, the purpose of the present invention, starting from the prior art mentioned above, is to provide a method for machine diagnosis, and especially for transmission diagnosis, which selectively detects ferrous wear and which enables on-line diagnosis indicating the condition of the machine or transmission. In addition, a device for implementing the method should be indicated.

SUMMARY OF THE INVENTION

The measurement system according to the invention consists of a capturing magnet with an arranged oppositely parallel reed contact. The measuring system is built into a oil duct of a machine or transmission. The oil stream flowing in the duct is contaminated with ferromagnetic particles. The local distribution of these particles is immaterial for the function of the sensor. On the lower side of the oil duct, there is a capturing magnet which collects the ferritic wear particles from the oil. The capturing magnet is so positioned in the oil duct so that the ferritic wear particles can accumulate on it. Due to the accumulation of ferritic wear particles, the magnetic flux, which passes through a reed contact, changes. The reed contact is positioned opposite the capturing magnet and is closed or open, depending on the level of the magnetic flux.

As soon as a certain quantity of ferritic wear particles have accumulated on the capturing magnet, a magnetic short-circuit results. This means that the magnetic field lines run, via the accumulated ferritic wear particles, directly from the North to the South pole of the capturing magnet. In other words, the magnetic field is screened from the reed contact. As a result, the reed contact opens at a defined threshold value. The threshold value depends on the quantity of accumulated iron particles. Since the quantity of particles can become very large, the reed contact must be arranged such that the magnetic scatter fields of the particles are reduced to a minimum. Otherwise, the capturing magnet is in effect extended towards the reed contact and the flux change is undetectable. The definition of the threshold value establishes when maintenance or checking of the transmission is necessary. Switching of the reed contact produces a binary datum with which the need for maintenance or checking can be associated.

Other advantages of the device according to the invention are as follows:

its mode of operation does not depend on the transport fluid;

its mode of operation does not depend on the duct cross-section, its mode of operation is largely independent of the Reynolds number of the transport fluid and of air included in it, the structure of the device is robust and it therefore has a long life.

production and operating costs are low; and on-line transmission or machine diagnosis is possible.

The binary measurement signal of the device, according to the invention, serves as a timely indication of high wear of ferritic moving parts of a transmission or a machine. This information can be used as a warning, which detects not yet visible damage and prevents a possible future total failure of the transmission or machine. Both repair costs/repurchasing of the transmission or machine and even a possible loss of earnings, for vehicles used commercially, can be reduced considerably by the device according to the invention. Moreover, the device, according to the invention, used, for example, in a transmission of a motor vehicle, can increase safety by avoiding transmission damage while driving.

BRIEF DESCRIPTION OF THE DRAWING

The invention will now be described, by way of example, with reference to the accompanying drawings in which.

DETAILED DESCRIPTION OF THE INVENTION

Figure 1:
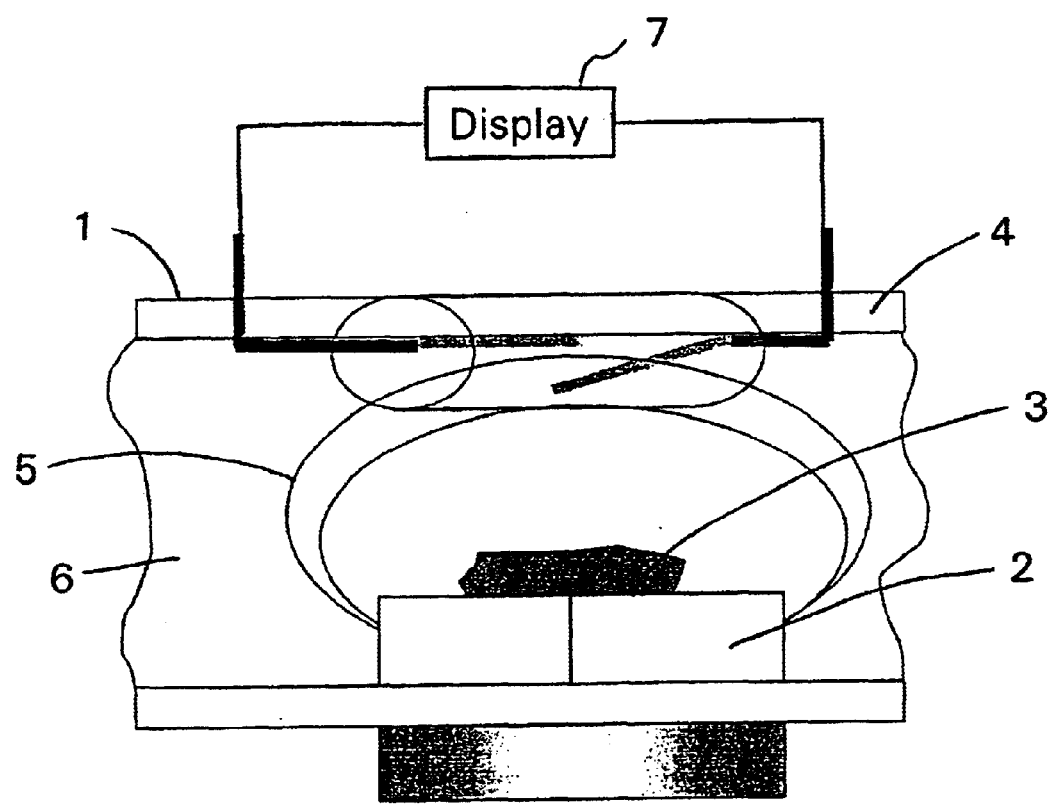
FIG. 1 shows a longitudinal section through part of an oil duct of a transmission.

The Figure shows a longitudinal section through part of an oil duct 4 of a transmission. A capturing magnet or permanent magnet 2 is arranged on the lower side of the oil duct 4. Opposite this permanent magnet 2, on the upper side of the oil duct 4, is a reed contact 1. As shown in the Figure, the magnetic field lines 5 emerge from the permanent magnet 2 and extend outwards through the cross-section of the oil duct. Ferritic wear particles 3, in the oil stream 6, are attracted by the permanent magnet 2 and accumulate on its surface. If enough ferritic wear particles 3 are present on the surface of the permanent magnet 2, the magnetic field lines run directly through the ferritic wear particles 3 from the North to the South pole. The result of this is that the density of the magnetic field lines, the so-termed magnetic flux density, decreases in the cross-section of the oil duct 4. This change of the magnetic flux density is detected by the reed contact 1 and, when its value exceeds or falls below a certain threshold value, the reed contact respectively opens or closes. The switching of the reed contact generates a binary measurement signal which is suitable for indicating that the condition of the transmission should be checked.

As shown in FIG. 1, the reed contact 1 is connected, in a conventional manner, to a display 7, a computer screen, an indicator, a warning light, etc., to indicate to the operator of the machine or the transmission that servicing of the machine or transmission is desired or necessary.

Reference Numerals
1. Reed contact
2. Capturing magnet
3. Ferritic wear particles
4. Oil duct
5. Magnetic field lines
6. Oil flow

What is claimed is:

1. A method for diagnosing a transmission of a motor vehicle by analyzing oil flowing within the transmission and detecting ferritic wear particles which accumulate within the oil during operation of the transmission, the method comprising the steps of:

placing a reed contact (1) in an upper region of an oil duct (4) of the transmission and locating a capturing magnet (2), opposite from the reed contact (1), in a lower region of the oil duct (4);

accumulating the ferritic wear particles on the capturing magnet (2) and producing a magnetic flux density, via the capturing magnet (2), over a cross-section of the oil duct (4) with the magnetic flux density changing due to accumulation of the ferritic wear particles (2) on a surface of the capturing magnet (2);

using a sensor, built into an oil duct (4) of the transmission, as part of the measurement system;

detecting the change in the magnetic flux density by the reed contact (1) and producing an output signal from the reed contact (1) which is indicative of a condition of the transmission for determining when serving of the transmission is necessary; and displaying, via an indicator, that servicing of the transmission is required.

2. A method for diagnosing a machine by analysis of oil flowing within the machine to detect ferritic wear particles accumulated within the oil, the method comprising the steps of:

placing a magnetic flux sensor in an first region of an oil duct of the machine and locating a capturing magnet in a second region of the oil duct wherein the capturing magnet produces a magnetic flux density in a cross section of the oil duct including the first region such that the magnetic flux sensor is held in a first state;

accumulating the ferritic wear particles on the capturing magnetic wherein the magnetic flux density in the first region changes with an accumulation of the ferritic wear particles on the capturing magnet; and detecting when the accumulation of ferritic wear particles reaches a certain amount when the resulting change in the magnetic flux density causes the magnetic flux sensor to change from the first state to a second state.

3. The method according to claim 2 further comprising the step of using a reed contact as the magnetic flux sensor.

4. The method according to claim 2 further comprising the step of using a transmission as the machine.

5. The method according to claim 2 further comprising the step of locating the first region is in an upper part of the oil duct, and locating the second region is in a lower part of the oil duct.

6. The method according to claim 2 further comprising the step of indicating, with a change in the magnetic flux sensor from the first stats to the second state, that servicing of the machine is indicated.

7. The method according to claim 2 further comprising the step of adjusting an effectiveness and a sensitivity of the sensor by virtue of positioning and technical characteristics of the capturing magnet and the magnetic flux sensor to adapt the system for a different environment.

8. A device for diagnosing a machine by analysis of oil flowing within the machine to detect ferritic wear particles accumulated within the oil, the device comprising:

a magnetic flux sensor located in an first region of an oil duct of the transmission and a capturing magnet located in a second region of the oil duct, wherein the capturing magnet produces a magnetic flux density in a cross section of the oil duct including the first region such that an initial magnetic flux density in the first region is sufficient to hold the magnetic flux sensor in a first state; and ferritic wear particles accumulate on the capturing magnetic such that the magnetic flux density in the first region changes with an accumulation of the ferritic wear particles on the capturing magnet; and the magnetic flux sensor indicates when the accumulation of ferritic wear particles reaches a certain amount when the resulting change in the magnetic flux density causes the magnetic flux sensor to change from the first state to a second state.

9. The device according to claim 8 wherein the magnetic flux sensor is a reed contact.

10. The device according to claim 8 wherein the machine is a transmission.

11. The device according to claim 8 wherein the first region is in an upper part of the oil duct, and the second region is in a lower part of the oil duct.

12. The device according to claim 8 wherein a change in the magnetic flux sensor from the first state to the second state indicates that servicing of the machine is indicated.

* * * * *